United States Patent [19]

Kraman

[11] Patent Number: 4,732,159
[45] Date of Patent: Mar. 22, 1988

[54] SIMPLE CAPSULE PNEUMOGRAPH

[75] Inventor: Steve S. Kraman, Lexington, Ky.

[73] Assignee: University of Kentucky Research Foundation, Lexington, Ky.

[21] Appl. No.: 858,694

[22] Filed: May 2, 1986

[51] Int. Cl.$^4$ .............................................. A61B 5/08
[52] U.S. Cl. ................................................... 128/721
[58] Field of Search ............... 128/716, 721, 722, 671; 381/67

[56] References Cited

U.S. PATENT DOCUMENTS

| | | | |
|---|---|---|---|
| 2,699,465 | 1/1955 | Hamilton | 381/67 |
| 3,658,052 | 4/1972 | Alter | 128/721 |
| 3,727,606 | 4/1973 | Sielaff | 128/722 |
| 3,782,368 | 1/1974 | Reibold | 128/687 |
| 3,831,586 | 8/1974 | Petit | 128/721 |
| 4,169,462 | 10/1979 | Strube | 128/721 |
| 4,245,651 | 1/1981 | Frost | 128/721 |
| 4,534,058 | 8/1985 | Hower | 381/67 |
| 4,598,417 | 7/1986 | Deno | 381/67 |

OTHER PUBLICATIONS

"Long Term Respiration Monitoring in Infants—A Comparison of Impedance and Pressure Capsule Monitors" by R. Railton et al., Clin. Phys. Physiol. Meas., 1983, 4(1); 91–94.

Primary Examiner—Edward M. Coven
Assistant Examiner—J. P. Lacyk
Attorney, Agent, or Firm—Birch, Stewart, Kolasch & Birch

[57] ABSTRACT

A capsule pneumograph includes an electret microphone connected to a capsule chestpiece attached to a sleeping subject. The output of the microphone is connected to the input of a recorder or monitor in order to provide a system for the detection of respiratory movements in subjects during polysomnographic sleep monitoring. A tube connecting the capsule chestpiece to the microphone functions as a low pass filter to pass only low frequency signals in the range of respiratory movements from the chestpiece to the microphone.

9 Claims, 8 Drawing Figures

SIMPLE CAPSULE PNEUMOGRAPH

BACKGROUND OF THE INVENTION

The present invention relates to a pneumograph, which is an instrument for sensing and measuring respiratory movements. More particularly, the present invention relates to the design and operation of a capsule pneumograph utilized for the detection of respiratory movements in subjects during polysomnographic sleep monitoring.

The pneumograph has been in use for years, with its usual construction being in the form of a rubber bellows connected to a chain or strap that encircles the chest so that respiratory movements expand and contract the bellows. The expansion and contraction of the bellows causes the pressure within the bellows to fall and rise in proportion to the chest excursion. The variations in pressure are sensed by a pressure transducer connected to the bellows by a tube.

The bellows pneumograph produces adequate results where an application requires knowledge of the phase and frequency, but not the precise depth, of respiration. Specifically, since this pneumograph encircles only the chest or abdomen, it can respond to movements in only one direction of a system that has two degrees of freedom. Also, the bellows pneumograph must be used with subjects in relatively fixed positions because uncontrolled body movements may increase or decrease the resting tension in the bellows, thus, changing the base line of the recording or even driving the transducer out of its useful range. If the strap slips, the respiratory movements may cease to be recorded at all. Another disadvantage of a bellows pneumograph is that a subject in a recumbent position may experience discomfort from lying on the chain, the strap or the bellows and, thus, have his freedom of movement limited. For these reasons, the bellows pneumograph has found little acceptance in sleep laboratories.

The prior art also includes the recent development of an apnea monitor that uses a pressure capsule as a motion sensor for use in the monitoring of infants. This development is described in "Long Term Respiration Monitoring in Infants—A Comparison of Impedance and Pressure Capsule Monitors" by R. Railton et al, Clin. Phys. Physiol. Meas., 1983; 4(1); 91-94.

SUMMARY OF THE INVENTION

The primary object of the present invention is to provide a pressure capsule pneumograph which is simply constructed and conveniently used on sleeping subjects with little discomfort or restriction of sleeping position. In this regard, it is an object of the present invention to provide a system for the detection of respiratory movements in adults during polysomnographic sleep monitoring.

It is a further object of the present invention to provide a device that, compared to the bellows pneumograph, is immune to base line shifts that are induced by body movements and is very simple to place on the subject, requiring no calibration.

It is an additional object of the present invention to provide a system that is less costly and is less complex than the known systems.

These and other objects of the present invention are fulfilled by providing a simple capsule pneumograph wherein an inexpensive electret condenser microphone is utilized. The microphone is connected to a small pressure capsule in such a way that it produces a reliable, easily interpreted and noise resistant signal reflecting respiratory movements of the chest wall or abdomen, depending on placement.

The design of the present invention is intended to accentuate the intrinsic low frequency response in the range of approximately 2-20 Hz. of the electret condenser microphone and diminish its higher frequency response above 20 Hz. to about 10-15 KHz. Thus, heart sounds, lung sounds, muscle noises and room noises are virtually excluded. This is accomplished by separating the capsule from the microphone by a 25 to 40 cm. section of thin plastic tubing having an internal diameter of 1.4 mm. and an outside diameter of 1.9 mm., which behaves as a low pass filter by attenuating rapidly oscillating air movement. In this regard, generally, the thinner and longer the tube, the higher the impedance to high frequency noise signals. It is also noted that the cavity that is made up by the capsule, the tubing and the microphone enclosure must be air-tight (hermetically sealed) in order to preserve the desired frequency characteristics.

Thus, when the system is in use, as the skin under the capsule chestpiece tightens and relaxes slightly with breathing, the pressure within the system rises and falls. These pressure variations, although very small, are converted into electrical signals by the microphone element and may be displayed and/or recorded.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF PREFERRED EMBODIMENT

Figure 1:
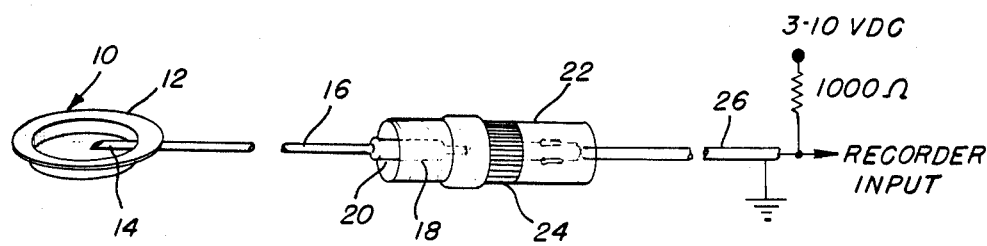
FIG. 1 is a schematic diagram of a simple capsule pneumograph according to the present invention.

Referring in detail to the drawings, there is illustrated in FIG. 1 a pressure capsule pneumograph constructed in accordance with the invention using widely available, inexpensive components. The capsule chestpiece 10 is a rigid circular shallow plastic cup with a flange 12. The dimensions of the capsule, which are not critical, are 18 mm diameter and 3 mm depth. The capsule flange can be attached to the skin with a common double sided adhesive ECG tape ring.

One end 14 of a section of tubing 16 (Intramedic polyethylene tubing, PE-200, I.D. 1.4 mm, 0.D. 1.9 mm) is secured in a hole in the chestpiece 10 and fastened with a drop of cyanoacrylate adhesive (e.g. Superglue). This adhesive does not permanently fix the tubing to the chestpiece. A firm pull from the hole, which is just large enough to accept the tubing, will remove the tubing 16 for replacement should it become kinked or otherwise damaged.

The other end of the tubing section 16 is inserted into an opening in tip 20 of microphone housing 22. The housing 22 may be the anterior portion of the barrel of a 3 cc syringe (Stylex Syringe, cat. no. 7200, Pharmaseal Laboratories, Glendale, CA) cut approximately 4 cm from the top. The top opening may have to be dilated slightly in order to insert the tubing into the opening. After insertion, the tubing is fixed in place with another drop of cyanoacrylate adhesive and several strips of tape.

The microphone housing 22 contains a microphone 24 which is an electret microphone, for example Radio Shack Model #270-090, which is wrapped in a layer of plastic electrical tape in order to fit snugly into the housing 22. The microphone is connected to a voltage source and the input of a recorder or display device by a shielded cable 26. The power requirements of the capsule pneumograph are those of the microphone, that is, 3 to 10 volts DC and a maximal current drain of 1 milliampere. The output signal is approximately 0.2 v peak-to-peak. This is sufficient amplitude to be displayed on any common oscilloscope, strip chart or instrumentation recorder with little or no additional amplification. No filtering or waveform processing is necessary.

The intrinsic low frequency response of the electret condenser microphone 24 is accentuated and its high frequency response is diminished by making the tubing section 16 between the capsule chestpiece 10 and the microphone 24 from 25 to 40 cm in length so that this tubing behaves as a low pass filter by attenuating rapidly oscillating air movement.

DESCRIPTION OF OPERATION

In operation, the device is very sensitive and provides a useful signal from almost any location on the lower chest or upper abdomen. The site that has been found to provide the most consistently satisfactory signal is the right upper abdomen, immediately below the right costal margin. Although experience with infants has been more limited, virtually any location on the anterior or posterior abdomen or chest wall of the infant yields large deflections during tidal breathing. Cardiac artifact is virtually absent in the use of the present invention.

In order to monitor the subject, the chestpiece 10 is attached to the skin with a double adhesive ring and also covered with a strip of tape. In addition, the tubing section 16 is taped down so that it is not pulled loose or damaged during sleep.

As the skin under the chestpiece 10 tightens and relaxes slightly with breathing the pressure within the chestpiece rises and falls. These pressure variations are transmitted to the microphone housing 22 by the tubing 16. Although the pressure variations are very small, they are converted into electrical signals by the microphone 24 and may be displayed and/or recorded.

FIGS. 2A, 2B, 2C and 2D show the data obtained from a subject during tidal breathing by utilizing the present invention, a bellows pneumograph and a pheumotachograph.

Figure 2A:
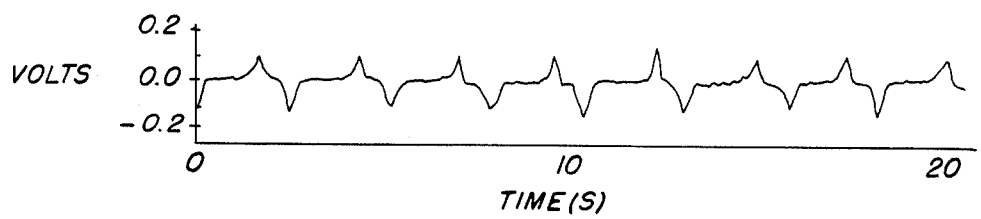
FIG. 2A is a graph showing a curve of pressure signals recorded by a recorder connected to a capsule pneumograph of the present invention.
Figure 2B:
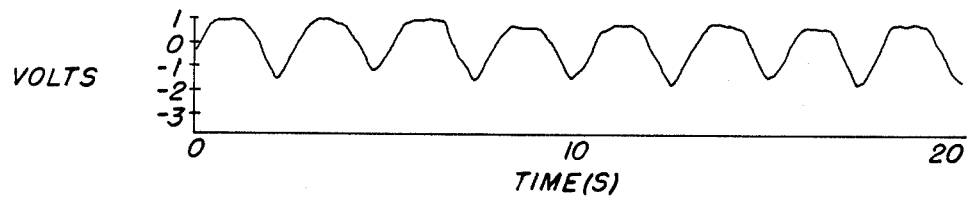
FIG. 2B is a graph showing a curve of pressure signals recorded by a recorder connected to a bellows pneumograph.
Figure 2C:
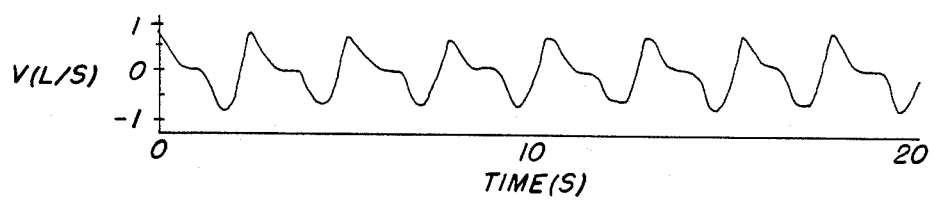
FIG. 2C is a graph showing a curve of an airflow signal recorded by a recorder connected to a Fleisch pneumotachograph.
Figure 2D:
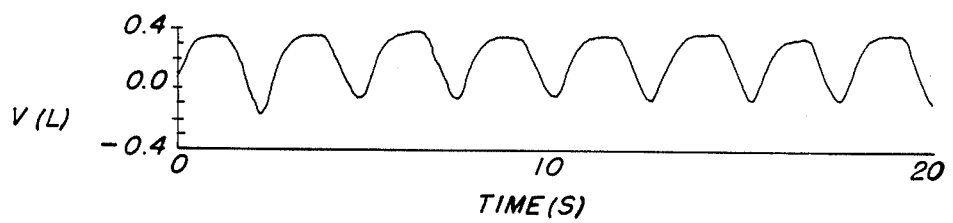
FIG. 2D is a graph of the air volume calculated from the air flow signal shown in FIG. 2C by integration.

FIG. 2A illustrates a graph showing a signal obtained with a capsule pneumograph of the present invention, while FIG. 2B illustrates a graph obtained with a bellows pneumograph. The capsule pneumograph was placed below the right costal margin and is shown to produce a usable signal. The bellows pneumograph was placed around the chest and connected to a pressure transducer (Stratham model 14159). The subject was semi-recumbent and breathed quietly through a Fleisch pneumotachograph which produced the airflow graph illustrated in FIG. 2C. The air volume illustrated in the graph of FIG. 2D was calculated from the airflow signal illustrated in FIG. 2C by integration.

Since the capsule pneumograph detects only local movement of the chest or abdomen, it is incapable of measuring indices of ventilation accurately. Thus, a second device must be used to detect ventilation, because the cessation of ventilation is the hallmark of apnea. It is known that the rectified and integrated laryngeal sound signal may be used as an index of airflow. In this regard, the combination of capsule pneumograph, laryngeal microphone and ear oximeter has been utilized as a simplified screening combination in a sleep laboratory.

Figure 3A:
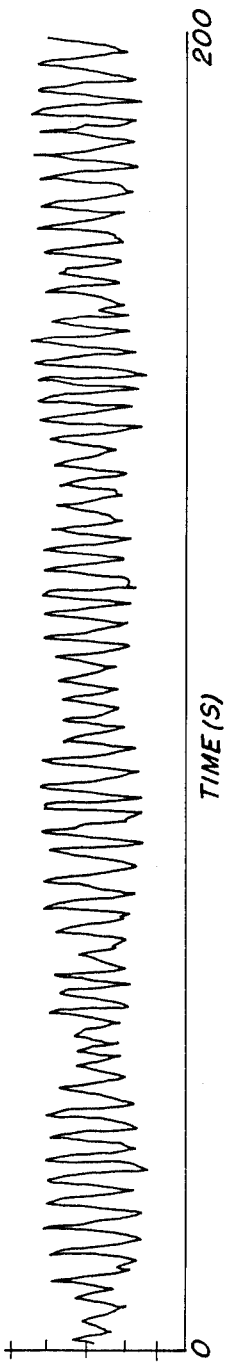
FIG. 3A is a graph showing the output obtained from a capsule pneumograph during sleep study of a patient.
Figure 3B:
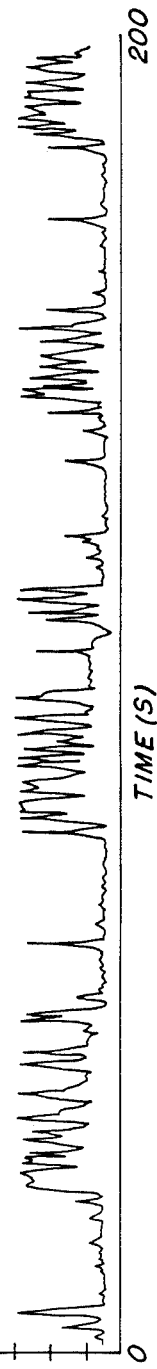
FIG. 3B is a graph showing the output obtained from a laryngeal sound envelope during sleep study of the same patient.
Figure 3C:
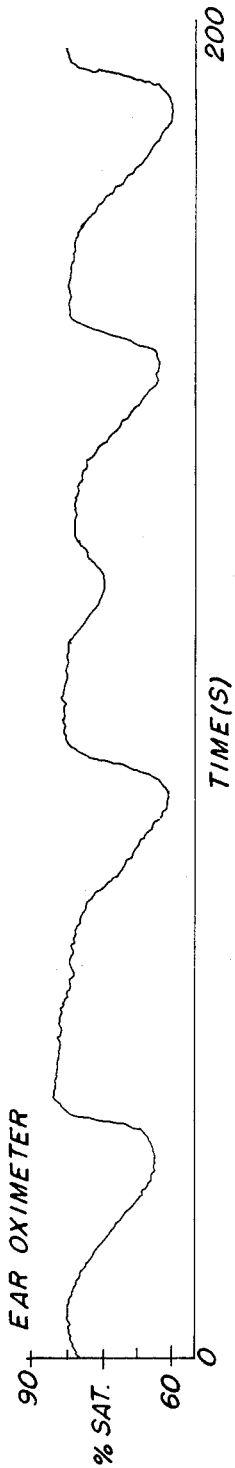
FIG. 3C is a graph showing the output obtained from an ear oximeter during sleep study of the same patient.

FIGS. 3A, 3B and 3C illustrate capsule pneumograph, laryngeal microphone and ear oximeter outputs respectively during sleep study in a patient with obstructive sleep apnea established by standard polysomnography. The monitoring is displayed in a time compressed format. The three signals were recorded on an instrumentation tape recorded (Hewlett Packard model 3964A) at a tape speed of 15/32 inches/sec. After completion of the study, the tape was played back at 32 times the original recording speed, digitized and displayed on a multichannel waveform analyzer (Data 6000, Data Precision Corp.) on a compressed time base. Four apneas, each approximately 30 seconds long, are apparent on the laryngeal microphone channel. Respiratory movements continued during the apneas as shown by the capsule pneumograph.

The capsule pneumograph using an electret microphone is comfortable, unobtrusive and minimally affected by changes in body position. It has performed satisfactorily on patients of all sizes and ages including obese adults and premature infants. In addition, the performance has been consistent regardless of the positions assumed by the patient during sleep, or the degree of restlessness of the patient.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

I claim:

1. A capsule pneumograph for detecting respiratory movement of a patient comprising:
   (a) capsule means adapted to be interfaced with the skin of the patient at a selected position on the patient's body which entraps a quantity of air between said capsule means and said patient's skin, said quantity of air expanding or contracting in response to respiratory movements which cause expansion and contraction of the interfaced skin;
   (b) a hermetically sealed microphone housing;

(c) tube means coupling the capsule means and hermetically sealed microphone housing into fluid communication with each other so that air pressure changes associated with the expansion and contraction of said entrapped air are transmitted as pressure signals from said capsule means to said microphone housing, the length and diameter of said tube means being selected to cause said tube means to pass pressure signals in a low frequency range associated with the frequency range of said respiratory movements and to block high frequency noise signals above said low frequency range; and (d) electric microphone means disposed in said microphone housing for sensing the pressure signals in the low frequency range and generating output signals indicative thereof.

2. A capsule pneumograph according to claim 1, wherein said microphone housing is a cylindrical member.

3. A capsule pneumograph according to claim 2, wherein said cylindrical member has one end wall with said tube means passing through an opening in said end wall.

4. A capsule pneumograph according to claim 1, wherein said microphone is an electret condenser microphone.

5. A capsule pneumograph according to claim 1, wherein said capsule means is formed as a circular shallow cup having an open end with a flange around said open end for contacting the skin to entrap air in said cup.

6. A capsule pneumograph according to claim 5, wherein said cup has an annular side wall and said tube means passes through an opening in said side wall.

7. A capsule pneumograph according to claim 1, wherein said tube means has a length of 25 to 40 cm.

8. A capsule pneumograph according to claim 1, wherein said tube means has an internal diameter of 1.4 mm.

9. A capsule pneumograph according to claim 7, wherein said tube means has an internal diameter of 1.4 mm.

* * * * *